US006793918B2

(12) United States Patent
Enholm et al.

(10) Patent No.: US 6,793,918 B2
(45) Date of Patent: Sep. 21, 2004

(54) IN VIVO STIMULATION OF ANGIOGENIC ACTIVITY

(75) Inventors: Berndt Enholm, Helsinki (FI); Didier Branellec, Lyons (FR); Seppo Ylae-Herttuala, Kuopio (FI); Ralf Pettersson, Stockholm (SE); Erika Bergsten, Stockholm (SE); Ulf Eriksson, Stockholm (SE); Kari Alitalo, Helsinki (FI); Aude Le Roux, Thiais (FR)

(73) Assignees: Ludwig Institute for Cancer Research, New York, NY (US); Licentia, Ltd., Helsinki (FI); Aventis Pharma SA, Antony (FR)

( * ) Notice: Subject to any disclaimer, the term of this patent is extended or adjusted under 35 U.S.C. 154(b) by 0 days.

(21) Appl. No.: 09/985,159

(22) Filed: Nov. 1, 2001

(65) Prior Publication Data

US 2003/0165464 A1 Sep. 4, 2003

Related U.S. Application Data

(60) Provisional application No. 60/244,598, filed on Nov. 1, 2000.

(51) Int. Cl.$^7$ .................. A61K 48/00; A01N 63/00; C12N 15/86; C07H 21/04
(52) U.S. Cl. ................ 424/93.2; 435/456; 435/320.1; 536/23.1
(58) Field of Search .................. 424/93.2, 93.21; 435/320.1, 455–457; 536/23.1, 23.5

(56) References Cited

U.S. PATENT DOCUMENTS

| 5,792,453 | A | * | 8/1998 | Hammond et al. ...... 424/93.21 |
| 5,928,939 | A | * | 7/1999 | Eriksson et al. ............ 435/325 |
| 5,932,540 | A | * | 8/1999 | Hu et al. ........................ 514/2 |
| 6,121,246 | A | * | 9/2000 | Isner ............................ 514/44 |
| 6,329,348 | B1 | * | 12/2001 | Crystal et al. ................ 514/44 |

FOREIGN PATENT DOCUMENTS

WO    WO 98/07832    * 2/1998

OTHER PUBLICATIONS

Dang et al. Gene therapy and translational cancer research. Clin. Cancer Res. 5:471–474, 1999.*

Deonarain, M.P. Ligand–targeted receptor–mediated vectors for gene therapy. Exp. Opin. Ther. Patents 8:53–69, 1998.*

Verma et al. Gene therapy: promises, problems and prospects. Nature 389:239–242, 1997.*

* cited by examiner

*Primary Examiner*—David Guzo
*Assistant Examiner*—Quang Nguyen
(74) *Attorney, Agent, or Firm*—Crowell & Moring LLP

(57) ABSTRACT

Angiogenesis is stimulated by introducing two replication-deficient adenovirus vectors to the endothelial cells or proximate to the endothelial cells of an organism. The first vector encodes VEGF-B$_{167}$ or a fragment or conservative substitution thereof, the second vector encodes VEGF-A or VEGF-C, or fragments or conservative substitutions thereof.

24 Claims, 3 Drawing Sheets

SEQUENCE LISTING

<160> NUMBER OF SEQ ID NOS: 2

<210> SEQ ID NO 1
<211> LENGTH: 18
<212> TYPE: DNA
<213> ORGANISM: Unknown
<220> FEATURE:
<223> OTHER INFORMATION: PCR forward primer

<400> SEQUENCE: 1
cgatctggcc atacactt                                                 18

<210> SEQ ID NO 2
<211> LENGTH: 25
<212> TYPE: DNA
<213> ORGANISM: Unknown
<220> FEATURE:
<223> OTHER INFORMATION: PCR reverse primer

<400> SEQUENCE: 2
ctatggatcc tcaccttcgc agctt                                         25

IN VIVO STIMULATION OF ANGIOGENIC ACTIVITY

This application claims the priority of U.S. Provisional Patent Application No. 60/244,598, filed on Nov. 1, 2000, the disclosure of which is expressly incorporated by reference herein.

BACKGROUND OF THE INVENTION

The present invention relates generally to gene therapy, more specifically, to virus-mediated and other forms of gene therapy. More particularly, the invention relates to adenovirus-mediated delivery of genes useful in the promotion of angiogenesis.

Angiogenesis is the formation of new capillary blood vessels by a process of sprouting from pre-existing vessels, and occurs during development as well as in a number of physiological and pathological processes. Angiogenesis is a physiologically complex process involving proliferation of endothelial cells, degradation of extracellular matrix, branching of vessels and subsequent cell adhesion events. In the adult, angiogenesis is tightly controlled and limited under normal circumstances to the female reproductive system. Angiogenesis can, however, be switched on in response to tissue damage. Solid tumors are also able to induce angiogenesis in surrounding tissue, thus sustaining tumor growth and facilitating the formation of metastases (Folkman, J., Nature Med. 1:27–31, (1995)). The molecular mechanisms underlying the complex angiogenic processes are far from being understood. A similar although far less well studied process also occurs in the lymphatic system, and is sometimes referred to as lymphangiogenesis.

Angiogenesis begins with localized breakdown of the basement membrane of the parent vessel, which is followed by the migration and outgrowth of endothelial cells into the surrounding extracellular matrix, resulting in the formation of a capillary sprout. A lumen is subsequently formed, and constitutes an essential element in functional sprout formation. Sprout maturation is completed after reconstitution of the basement membrane.

Alterations in at least three endothelial cell functions occur during this series of events: 1) modulation of interactions with the extracellular matrix, which requires alterations in cell-matrix contacts and the production of matrix-degrading proteolytic enzymes (plasminogen activators (PAs) and matrix metalloproteinases); 2) an initial increase and subsequent decrease in locomotion (migration), which allows the cells to translocate towards the angiogenic stimulus and to stop once they reach their destination; 3) an increase in proliferation, which provides new cells for the growing and elongating vessel, and a subsequent return to the quiescent state once the vessel is formed.

Together, these cellular functions contribute to the process of capillary morphogenesis, i.e. the formation of three-dimensional patent or open tube-like structures. Many newly formed capillaries subsequently undergo a process of vessel wall maturation (i.e. formation of a smooth muscle cell-rich media and an adventitia, while others undergo regression (i.e. in the absence of blood flow) [see Pepper et al., *Enzyme Protein*, 49:138–162 (1996); Risau, *Nature* 386:671–674 (1997)].

With the exception of angiogenesis which occurs in response to tissue injury or in female reproductive organs, endothelial cell turnover in the healthy adult organism is very low. The maintenance of endothelial quiescence is thought to be due to the presence of endogenous negative regulators, since positive regulators are frequently detected in adult tissues in which there is apparently no angiogenesis. The converse is also true, namely that positive and negative regulators often co-exist in tissues in which endothelial cell turnover is increased. This has lead to the notion of the "angiogenic switch", in which endothelial activation status is determined by a balance between positive and negative regulators.

In activated (angiogenic) endothelium, positive regulators predominate, whereas endothelial quiescence is achieved and maintained by the dominance of negative regulators [Hanahan et al., *Cell*, 86:353–364 (1996)]. Used initially in the context of tumor progression to describe the passage from the prevascular to the vascular phase, the notion of the "switch" can also be applied in the context of developmental, physiological as well as pathological angiogenesis. Although it still remains to be definitively demonstrated in vivo, the current working hypothesis is that the "switch" involves the induction of a positive regulator and/or the loss of a negative regulator.

Because of the crucial role of angiogenesis in so many physiological and pathological processes, factors involved in the control of angiogenesis have been intensively investigated. A number of growth factors have been shown to be involved in the regulation of angiogenesis; these include fibroblast growth factors (FGFs), platelet-derived growth factors (PDGFs), transforming growth factor alpha (TGF-alpha), and hepatocyte growth factor (HGF). See for example Folkman et al., *J. Biol. Chem.*, 267:10931–10934 (1992) for a review.

It has been suggested that a particular family of endothelial cell-specific growth factors, the vascular endothelial growth factors (VEGFs), and their corresponding receptors is primarily responsible for stimulation of endothelial cell growth and differentiation, and for certain functions of the differentiated cells. These factors are members of the PDGF/VEGF family, and appear to act primarily via endothelial receptor tyrosine kinases (RTKs). The PDGF/VEGF family of growth factors belongs to the cystine-knot superfamily of growth factors, which also includes the neurotrophins and transforming growth factor-$\beta$.

Eight different proteins have been identified in the PDGF/VEGF family, namely two PDGFs (A and B), VEGF-A and five members that are closely related to VEGF-A. The five members closely related to VEGF-A are: VEGF-B, described in International Patent Application PCT/US96/02957 (WO 96/26736) and in U.S. Pat. Nos. 5,840,693 and 5,607,918 by Ludwig Institute for Cancer Research and The University of Helsinki; VEGF-C or VEGF2, described in Joukov et al., *EMBO J.* 15:290–298 (1996), Lee et al., *Proc. Natl. Acad. Sci. USA* 93:1988–1992 (1996), and U.S. Pat. Nos. 5,932,540 and 5,935,540 by Human Genome Sciences, Inc; VEGF-D, described in International Patent Application No. PCT/US97/14696 (WO 98/07832), and Achen et al., *Proc. Natl. Acad. Sci. USA* 95:548–553 (1998); the placenta growth factor (PlGF), described in Maglione et al., *Proc.*

Natl. Acad. Sci. USA 88:9267–9271 (1991); and VEGF3, described in International Patent Application No. PCT/US95/07283 (WO 96/39421) by Human Genome Sciences, Inc.

Each VEGF family member has between 30% and 45% amino acid sequence identity with VEGF-A in their VEGF homology domain (VHD). This VHD contains the eight conserved cysteine residues which form the cystine-knot motif. In their active, physiological state, the proteins are dimers. Functional characteristics of the VEGF family include varying degrees of mitogenicity for endothelial cells and related cell types, induction of vascular permeability and angiogenic and lymphangiogenic properties.

Vascular endothelial growth factor (VEGF-A) is a homodimeric glycoprotein that has been isolated from several sources. VEGF-A shows highly specific mitogenic activity for endothelial cells. VEGF-A has important regulatory functions in the formation of new blood vessels during embryonic vasculogenesis and in angiogenesis during adult life (Carmeliet et al., *Nature,* 380: 435–439, (1996); Ferrara et al., *Nature,* 380: 439–442, (1996); reviewed in Ferrara and Davis-Smyth, *Endocrine Rev.,* 18: 4–25, (1997)). The significance of the role played by VEGF-A has been demonstrated in studies showing that inactivation of a single VEGF-A allele results in embryonic lethality due to failed development of the vasculature (Carmeliet et al., *Nature,* 380: 435–439, (1996); Ferrara et al., *Nature,* 380: 439–442, (1996)). The isolation and properties of VEGF-A have been reviewed; see Ferrara et al., *J. Cellular Biochem.,* 47: 211–218, (1991) and Connolly, *J. Cellular Biochem.,* 47:219–223, (1991).

In addition VEGF-A has strong chemoattractant activity towards monocytes, can induce the plasminogen activator and the plasminogen activator inhibitor in endothelial cells, and can also induce microvascular permeability. Because of the latter activity, it is sometimes referred to as vascular permeability factor (VPF). VEGF-A is also chemotactic for certain hematopoetic cells. Recent literature indicates that VEGF-A blocks maturation of dendritic cells and thereby reduces the effectiveness of the immune response to tumors (many tumors secrete VEGF-A) (Gabrilovich et al., *Blood* 92: 4150–4166, (1998); Gabrilovich et al., *Clinical Cancer Research* 5:2963–2970, (1999)).

Vascular endothelial growth factor B (VEGF-B) has similar angiogenic and other properties to those of VEGF-A, but is distributed and expressed in tissues differently from VEGF-A. In particular, VEGF-B is very strongly expressed in heart, and only weakly in lung, whereas the reverse is the case for VEGF-A (Olofsson, B. et al., *Proc. Natl. Acad. Sci. USA* 93:2576–2581 (1996)). RT-PCR assays have demonstrated the presence of VEGF-B mRNA in melanoma, normal skin, and muscle. This suggests that VEGF-A and VEGF-B, despite the fact that they are co-expressed in many tissues, may have functional differences.

A comparison of the PDGF/VEGF family of growth factors reveals that the 167 amino acid isoform of VEGF-B is the only family member that is completely devoid of any glycosylation. Gene targeting studies have shown that VEGF-B deficiency results in mild cardiac phenotype, and impaired coronary vasculature (Bellomo et al., *Circ. Res.* 86:E29–35 (2000)). VEGF-B knock out mice were demonstrated to have impaired coronary vessel structure, smaller hearts and impaired recovery after cardiac ischemia (Bellomo, D. et al., *Circulation Research (Online),* 86:E29–35 (2000)).

Human VEGF-B was isolated using a yeast co-hybrid interaction trap screening technique by screening for cellular proteins which might interact with cellular retinoic acid-binding protein type I (CRABP-I). The isolation and characteristics including nucleotide and amino acid sequences for both the human and mouse VEGF-B are described in detail in PCT/US96/02957, in U.S. Pat. Nos. 5,840,693 and 5,607,918 by Ludwig Institute for Cancer Research and The University of Helsinki and in Olofsson et al., *Proc. Natl. Acad. Sci. USA* 93:2576–2581 (1996). The nucleotide sequence for human VEGF-B is also found at GenBank Accession No. U48801. The entire disclosures of the International Patent Application PCT/US97/14696 (WO 98/07832), U.S. Pat. Nos. 5,840,693 and 5,607,918 are incorporated herein by reference.

The mouse and human genes for VEGF-B are almost identical, and both span about 4 kb of DNA. The genes are composed of seven exons and their exon-intron organization resembles that of the VEGF and PlGF genes (Grimmond et al., *Genome Res.* 6:124–131 (1996); Olofsson et al., *J. Biol. Chem.* 271:19310–19317 (1996); Townson et al., *Biochem. Biophys. Res. Commun.* 220:922–928 (1996)).

VEGF-C was isolated from conditioned media of the PC-3 prostate adenocarcinoma cell line (CRL1435) by screening for ability of the medium to induce tyrosine phosphorylation of the endothelial cell-specific receptor tyrosine kinase VEGFR-3 (Flt4), using cells transfected to express VEGFR-3. VEGF-C was purified using affinity chromatography with recombinant VEGFR-3, and was cloned from a PC-3 cDNA library. Its isolation and characteristics are described in detail in Joukov et al., *EMBO J.,* 15: 290–298, (1996).

VEGF-D was isolated from a human breast cDNA library, commercially available from Clontech, by screening with an expressed sequence tag obtained from a human cDNA library designated "Soares Breast 3NbHBst" as a hybridization probe (Achen et al., *Proc. Natl. Acad. Sci. USA,* 95: 548–553, (1998)). Its isolation and characteristics are described in detail in International Patent Application No. PCT/US97/14696 (WO98/07832). In PCT/US97/14696, the isolation of a biologically active fragment of VEGF-D is also described. This fragment consists of VEGF-D amino acid residues 93 to 201.

The VEGF-D gene is broadly expressed in the adult human, but is certainly not ubiquitously expressed. VEGF-D is strongly expressed in heart, lung and skeletal muscle. Intermediate levels of VEGF-D are expressed in spleen, ovary, small intestine and colon, and a lower expression occurs in kidney, pancreas, thymus, prostate and testis. No VEGF-D mRNA was detected in RNA from brain, placenta, liver or peripheral blood leukocytes.

PlGF was isolated from a term placenta cDNA library. Its isolation and characteristics are described in detail in Maglione et al., *Proc. Natl. Acad. Sci. USA,* 88: 9267–9271, (1991). Presently its biological function is not well understood.

VEGF3 was isolated from a cDNA library derived from colon tissue. VEGF3 is stated to have about 36% identity and 66% similarity to VEGF. The method of isolation of the gene encoding VEGF3 is unclear and no characterization of the biological activity is disclosed in International Patent Application No. PCT/US95/07283 (WO 96/39421).

Similarity between two proteins is determined by comparing the amino acid sequence and conserved amino acid substitutions of one of the proteins to the sequence of the second protein, whereas identity is determined without including the conserved amino acid substitutions.

As noted above, the PDGF/VEGF family members act primarily by binding to receptor tyrosine kinases. In general, receptor tyrosine kinases are glycoproteins, which consist of an extracellular domain capable of binding a specific growth factor(s), a transmembrane domain, which is usually an alpha-helical portion of the protein, a juxtamembrane domain, which is where the receptor may be regulated by, e.g., protein phosphorylation, a tyrosine kinase domain, which is the enzymatic component of the receptor and a carboxy-terminal tail, which in many receptors is involved in recognition and binding of the substrates for the tyrosine kinase.

Five endothelial cell-specific receptor tyrosine kinases have been identified, belonging to two distinct subclasses: three vascular endothelial cell growth factor receptors, VEGFR-1 (Flt-1), VEGFR-2 (KDR/Flk-1), VEGFR-3 (Flt4), and the two receptors of the Tie family, Tie and Tie-2 (Tek). These receptors differ in their specificity and affinity. All of these have the intrinsic tyrosine kinase activity which is necessary for signal transduction.

The only receptor tyrosine kinases known to bind VEGFs are VEGFR-1, VEGFR-2 and VEGFR-3. VEGFR-1 and VEGFR-2 bind VEGF with high affinity, and VEGFR-1 also binds PlGF. VEGF-B binds to VEGFR-1 with high affinity, but not to VEGFR-2 or -3 (Olofsson et al., *Proc. Natl. Acad. Sci. USA*, 95:11709–11714 (1998)). VEGF-C has been shown to be the ligand for VEGFR-3, and it also activates VEGFR-2 (Joukov et al., *EMBO J.* 15:290–298 (1996)). VEGF-D binds to both VEGFR-2 and VEGFR-3 (Achen et al., *Proc. Natl. Acad. Sci. USA* 95:548–553 (1998)). A ligand for Tek/Tie-2 has been described in International Patent Application No. PCT/US95/12935 (WO 96/11269) by Regeneron Pharmaceuticals, Inc. The ligand for Tie has not yet been identified.

A novel 130–135 kDa VEGF isoform specific receptor has been purified and cloned (Soker et al., *Cell* 92:735–745 (1998)). The VEGF receptor was found to specifically bind the VEGF$_{165}$ isoform via the exon 7 encoded sequence, which shows weak affinity for heparin (Soker et al., *Cell* 92:735–745 (1998)). Surprisingly, the receptor was shown to be identical to human neuropilin-1 (NP-1), a receptor involved in early stage neuromorphogenesis. VEGF-B$_{167}$ also binds to NP-1 (Makinen, T. et al, *J Biol Chem.,* 274:21217–21222(1999)). In addition, PlGF-2 also appears to interact with NP-1 (Migdal et al., *J. Biol. Chem.* 273:22272–22278 (1998)).

VEGFR-1, VEGFR-2 and VEGFR-3 are expressed differently by endothelial cells. Generally, both VEGFR-1 and VEGFR-2 are expressed in blood vessel endothelia (Oelrichs et al., *Oncogene* 8:11–18 (1992); Kaipainen et al., *J. Exp. Med.* 178:2077–2088 (1993); Dumont et al., *Dev. Dyn.* 203:80–92 (1995); Fong et al., *Dev. Dyn.* 207:1–10 (1996)) and VEGFR-3 is mostly expressed in the lymphatic endothelium of adult tissues (Kaipainen et al., *Proc. Natl. Acad. Sci. USA* 9:3566–3570 (1995)). VEGFR-3 is also expressed in the blood vasculature surrounding tumors.

VEGFRs are expressed in many adult tissues, despite the apparent lack of constitutive angiogenesis. VEGFRs are however clearly upregulated in endothelial cells during development and in certain angiogenesis-associated/dependent pathological situations including tumor growth [see Dvorak et al., *Amer. J. Pathol.,* 146:1029–1039 (1995); Ferrara et al., *Endocrine Rev.,* 18:4–25 (1997)]. The phenotypes of VEGFR-1-deficient mice and VEGFR-2-deficient mice reveal an essential role for these receptors in blood vessel formation during development.

VEGFR-1-deficient mice die in utero at mid-gestation due to inefficient assembly of endothelial cells into blood vessels, resulting in the formation of abnormal vascular channels [Fong et al., *Nature,* 376:66–70 (1995)]. VEGFR-2-deficient mice die in utero between 8.5 and 9.5 days post-coitum, and in contrast to VEGFR-1, this appears to be due to abortive development of endothelial cell precursors [Shalaby et al., *Nature* 376:62–66 (1995)]. The importance of VEGFR-2 in tumor angiogenesis has also been clearly demonstrated by using a dominant-negative approach [Millauer et al., *Nature,* 367:576–579 (1994); Millauer et al., *Cancer Res.* 56:1615–1620 (1996)]. The phenotype of VEGFR-3-deficient mice has been reported in Dumont, et al., Cardiovascular Failure in Mouse Embryos Deficient in VEGF Receptor-3, *Science,* 282:946–949 (1998). VEGFR-3 deficient mice die in utero between 12 and 14 days of gestation due to defective blood vessel development.

Despite intensive activity in the art, there has remained a need for ways to stimulate angiogenesis in vivo.

SUMMARY OF THE INVENTION

The present invention is directed to a gene therapy approach useful in stimulation of angiogenesis. One objective of the present invention is to provide a method for stimulating angiogenesis in which VEGF-B$_{167}$ proteins or peptides in addition to other VEGF proteins and peptides as are produced to a therapeutically significant degree for sustained periods to stimulate angiogenesis with at least a first vector construct having a polynucleotide sequence for VEGF-B$_{167}$ and a second vector construct containing a polynucleotide sequence for another VEGF, preferably a replication-deficient adenovirus construct.

According to one embodiment of the present invention, a method of stimulating angiogenesis comprises introducing a first replication-deficient adenovirus vector comprising a polynucleotide sequence encoding VEGF-B$_{167}$ or a fragment or conservative substitution thereof to an organism and introducing a second replication-deficient adenovirus vector comprising a polynucleotide sequence encoding VEGF-A or a fragment or conservative substitution thereof to the organism. In this embodiment the replication-deficient adenovirus vectors are delivered to at least one cell of the organism, the target cell being either an endothelial cell or a cell in proximity to an endothelial cell.

According to a further embodiment, the target cells are vascular cells. According to a further embodiment, the target cells are either microvascular endothelial cells or aortic endothelial cells.

According to a further embodiment, the organism may be mammalian, murine, or human.

According to a further embodiment, $10^7$ to $10^{13}$ of vector particles of each adenovirus vector are introduced to the organism.

According to a further embodiment, expression of the polynucleotide sequence is driven by a CMV promoter which is contained in the vector.

According to a further embodiment of the present invention, a method of stimulating angiogenesis comprises introducing a first replication-deficient adenovirus vector comprising a polynucleotide sequence encoding VEGF-B$_{167}$ or a fragment or conservative substitution thereof to an organism and introducing a second replication-deficient adenovirus vector comprising a polynucleotide sequence encoding VEGF-C or a fragment or conservative substitution thereof to the organism. In this embodiment the replication-deficient adenovirus vectors are delivered to at least one cell of the organism, the target cell being either an endothelial cell or a cell in proximity to an endothelial cell.

According to a further embodiment of the present invention, a method of stimulating angiogenesis comprises introducing a first replication-deficient adenovirus vector comprising a polynucleotide sequence encoding VEGF-B$_{167}$ or a fragment or conservative substitution thereof to an organism and introducing a second replication-deficient adenovirus vector comprising a polynucleotide sequence encoding VEGF-D or a fragment or conservative substitution thereof to the organism. In this embodiment the replication-deficient adenovirus vectors are delivered to at least one cell of the organism, the target cell being either an endothelial cell or a cell in proximity to an endothelial cell.

The reasons for using a replication-deficient adenovirus construct are that it allows efficient in vivo expression of the transgene. The virus is produced to high titers and many cell types can be infected with adenovirus. It also allows for the simultaneous expression of more than one transgene by coinfection with the recombinant adenoviruses (e.g. VEGF-B+VEGF-A). Expression is also very fast, usually within 24–48 hours.

The method involves stimulating angiogenesis by delivering VEGF-B$_{167}$ and another VEGF to target cells of an organism in need of such stimulation. The target cells include, but are not limited to, endothelial cells or cells in the proximity of endothelial cells, vascular endothelial cells, microvascular endothelial cells and aortic endothelial cells. These cells can be from a mammalian organism, such as murine or human cells. Preferably the expression of the polynucleotide sequences is driven by a cytomegalovirus (CMV) promoter. Preferably about 107 to about 1013 of vector particles of each adenovirus vector are delivered in vivo.

Because the nude mouse has been proven to be a relevant animal model for angiogenesis, a similar effect can be expected in humans.

These recombinant adenoviruses can be administered as a pharmaceutical composition in combination with any standard physiologically and/or pharmaceutically acceptable carriers known in the art. The term "pharmaceutically acceptable" means a non-toxic material that does not interfere with the effectiveness of the biological activity of the active ingredients. The term "physiologically acceptable" refers to a non-toxic material that is compatible with a biological system such as a cell, cell culture, tissue or organism. The characteristics of the carrier will depend on the route of administration. Physiologically and pharmaceutically acceptable carriers include diluents, fillers, salts, buffers, stabilizers, solubilizers, and other materials which are well known in the art.

It is within the scope of the present invention to employ functional fragments of the desired sequences. Techniques known in the art may be employed to conserve the regions of the sequence necessary for proper function, while performing appropriate substitutions and/or deletions to the remaining portions of the sequence so that the resultant product maintains the function of the full sequence.

As used herein, the term "conservative substitution" denotes the replacement of an amino acid residue by another, biologically similar residue. Examples of conservative substitutions include the substitution of one hydrophobic residue such as isoleucine, valine, leucine, alanine, cysteine, glycine, phenylalanine, proline, tryptophan, tyrosine, norleucine or methionine for another, or the substitution of one polar residue for another, such as the substitution of arginine for lysine, glutamic acid for aspartic acid, or glutamine for asparagine, and the like. Neutral hydrophilic amino acids which can be substituted for one another include asparagine, glutamine, serine and threonine. The term "conservative substitution" also includes the use of a substituted amino acid in place of an unsubstituted parent amino acid.

As such, it should be understood that in the context of the present invention, a conservative substitution is recognized in the art as a substitution of one amino acid for another amino acid that has similar properties. Exemplary conservative substitutions are set out in the following Table A from WO 97/09433.

TABLE A

| Conservative Substitutions I | |
|---|---|
| SIDE CHAIN CHARACTERISTIC | AMINO ACID |
| Aliphatic | |
| Non-polar | G A P |
| | I L V |
| Polar - uncharged | C S T M |
| | N Q |
| Polar - charged | D E |
| | K R |
| Aromatic | H F W Y |
| Other | N Q D E |

Alternatively, conservative amino acids can be grouped as described in Lehninger, [Biochemistry, Second Edition; Worth Publishers, Inc. NY:NY (1975), pp.71–77] as set out in the following Table B.

TABLE B

Conservative Substitutions II

| SIDE CHAIN CHARACTERISTIC | AMINO ACID |
|---|---|
| Non-polar (hydrophobic) | |
| A. Aliphatic: | A L I V P |
| B. Aromatic: | F W |
| C. Sulfur-containing: | M |
| D. Borderline: | G |
| Uncharged-polar | |
| A. Hydroxyl: | S T Y |
| B. Amides: | N Q |
| C. Sulfhydryl: | C |
| D. Borderline: | G |
| Positively Charged (Basic): | K R H |
| Negatively Charged (Acidic): | D E |

Exemplary conservative substitutions are set out in the following Table C.

TABLE C

Conservative Substitutions III

| Original Residue | Exemplary Substitution |
|---|---|
| Ala (A) | Val, Leu, Ile |
| Arg (R) | Lys, Gln, Asn |
| Asn (N) | Gln, His, Lys, Arg |
| Asp (D) | Glu |
| Cys (C) | Ser |
| Gln (Q) | Asn |
| Glu (E) | Asp |
| His (H) | Asn, Gln, Lys, Arg |
| Ile (I) | Leu, Val, Met, Ala, Phe, |
| Leu (L) | Ile, Val, Met, Ala, Phe |
| Lys (K) | Arg, Gln, Asn |
| Met (M) | Leu, Phe, Ile |
| Phe (F) | Leu, Val, Ile, Ala |
| Pro (P) | Gly |
| Ser (S) | Thr |
| Thr (T) | Ser |
| Trp (W) | Tyr, Phe |
| Tyr (Y) | Trp, Phe, Thr, Ser |
| Val (V) | Ile, Leu, Met, Phe, Ala |

If desired, the peptides of the invention can be modified, for instance, by glycosylation, amidation, carboxylation, or phosphorylation, or by the creation of acid addition salts, amides, esters, in particular C-terminal esters, and N-acyl derivatives of the peptides of the invention. The peptides also can be modified to create peptide derivatives by forming covalent or noncovalent complexes with other moieties. Covalently-bound complexes can be prepared by linking the chemical moieties to functional groups on the side chains of amino acids comprising the peptides, or at the N- or C-terminus.

It is anticipated that the aforementioned peptides can be conjugated to a reporter group, including, but not limited to a radiolabel, a fluorescent label, an enzyme (e.g., that catalyzes a colorimetric or fluorometric reaction), a substrate, a solid matrix, or a carrier (e.g., biotin or avidin).

BRIEF DESCRIPTION OF THE DRAWINGS

The invention will be described in further detail hereinafter with reference to the accompanying drawings in which:

FIGS. 2B and 2E-AdVEGF,

FIGS. 2A and 2D-AdLacZ,

FIGS. 2C and 2F-AdVEGF-A+AdVEGF-B; and

DETAILED DESCRIPTION OF PREFERRED EMBODIMENTS

EXAMPLE 1

Production of Recombinant Adenovirus with VEGF-$B_{167}$ or VEGF-A

To make AdVEGF-$B_{167}$ vector, the full-length VEGF-$B_{167}$ cDNA was amplified from a plasmid by PCR (forward primer: 5' CGA TCT GGC CAT ACA CTT 3' (SEQ ID NO:1); reverse primer 5' CTA TGG ATC CTC ACC TTC GCA GCT T 3' (SEQ ID NO:2), contains a BamHI site) and then cloned into the TA-plasmid pCR2.1 vector (Invitrogen).

Following amplification in *E. coli* and plasmid purification, the insert was excised with BamHI and cloned into the BamHI site of the plasmid pQBI-AdCMV5-IRES-GFP (Quantum Biotechnologies, Quebec, Canada; transfer plasmid). In this plasmid the cDNA expression is driven from the CMV promoter. The plasmid also contains an IRES-element allowing the simultaneous expression of green fluorescent protein (GFP). Expression of VEGF-B was verified by transfecting the plasmid into COS-1 cells.

The above transfer plasmid was linearized with FseI and then cotransfected with pJM17, a circular adenovirus plasmid (Microbix Biosystems Inc, Ontario, Canada), into 293 cells. Transfection was with Lipofectamine Plus. Fourteen days later, cells were harvested, broken by freeze-thawing, and the supernatant from a low-speed centrifugation was used to infect new 293 cells. The amplification step was repeated once. Expression of the insert was verified using GFP as an indicator. After this, the recombinant virus was plaque-purified in 293 cells once using standard protocols. A GFP-positive plaque was amplified and subsequently used to prepare a stock that was purified by CsCl centrifugation.

To make the AdVEGF-A vector, full-length VEGF-A was cloned into a first-generation adenovirus vector described in Hiltunen et al., *Circulation*, 102:2262–2268 (2000). This reference is expressly incorporated by reference. Alternatively, active fragments of VEGF-A or either the entire or fragmented sequence containing conservative substitutions could be employed. The preparation of other vectors and the use of different vector preparation techniques known in the art are within the scope of the present invention. Further, the techniques employed to create the VEGF-$B_{167}$ or VEGF-A adenovirus vectors could be employed to create VEGF-C or VEGF-D adenovirus vectors.

293 EBNA cells were incubated for one hour in serum free media containing $2 \times 10^7$ pfu of AdVEGF-$B_{167}$.

Figure 1:
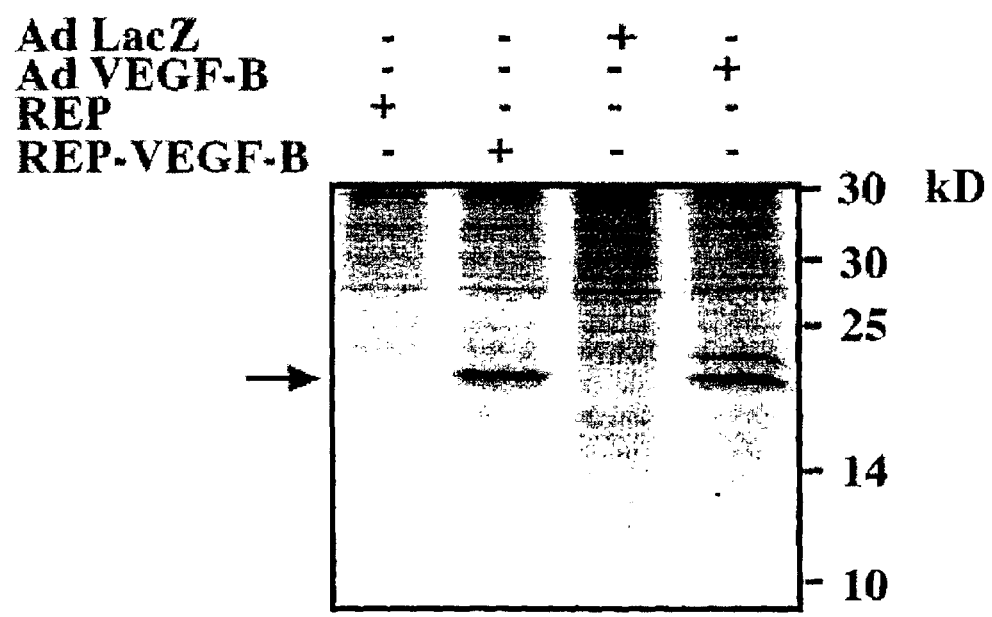
FIG. 1 represents a blot of an immunoprecitation of 293 EBNA cells infected with AdVEGF-$B_{167}$ using polyclonal antibodies against VEGF-B.
Figure 2:
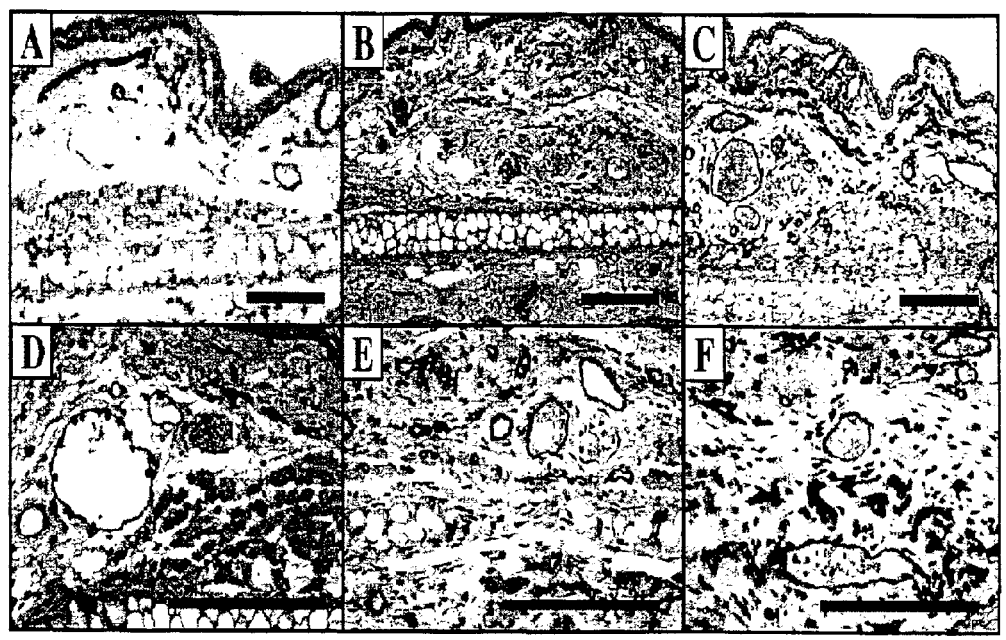
FIGS. 2A–2F show results of stained sections of the skin of mouse ears injected subcutaneously with the recombinant adenoviruses.

Additionally, cells were transfected with pREP7 (Invitrogen) plasmid expression vectors encoding VEGF-B or pREP7 vector control using the calcium phosphate method. Cells were metabolically labeled the next day with $S^{35}$-methionine and cysteine (Promix, Amersham) for 6 hours. The media were collected and labeled VEGF-B proteins were precipitated using a polyclonal antibody raised against VEGF-B [see Olofsson, B. et al, *Proc. Natl. Acad. Sci. USA*, 93:2576–2581 (1996)]. The precipitated proteins bound to protein A sepharose were washed three times in phosphate-buffered saline, dissolved in Laemmli sample buffer and analyzed on a 12.5% or 15% SDS-PAGE gel. Gels were then dried and analysed by a phoshoimager and autoradiography. As seen in FIG. 1, cells infected with the AdVEGF-$B_{167}$ or transfected with the pREC7 plasmids encoding VEGF-$B_{167}$ produced major polypeptides of about 21 kD.

EXAMPLE 2

Evaluation of Angiogenic Response to Recombinant Adenoviruses

About $2\times10^8$ pfu of each of the VEGF-$B_{167}$ and VEGF-A recombinant adenoviruses were injected subcutaneously into five ears of three NMRI nu/nu mice (Harlan, the Netherlands). The mice were sacrificed at various time points after infection and the skin from the site of injection was fixed in 4% paraformaldehyde and embedded in paraffin. Seven micrometer sections were stained with monoclonal antibodies against VEGFR-2 [Kataoka, H. et al. *Development Growth & Differentiation*, 39:729–740 (1997)] or the platelet endothelial cell adhesion molecule-1 (PECAM-1) (BD Pharmingen, San Diego, Calif., USA, cat.no. 01951D).

PECAM-1 is a 130-kD member of the immunoglobulin (Ig) superfamily that is a major constituent of the endothelial cell intercellular junction, where up to $10^6$ PECAM-1 molecules are concentrated. PECAM-1 is also expressed on the surface of circulating platelets, monocytes, neutrophils and selected T cell subsets. The tyramide signal amplification (TSA) kit (NEN Life Sciences, Boston, Me., USA) was used to enhance staining. Negative controls were produced by omitting the primary antibodies. The results were viewed with an Olympus AX80 microscope and photographed.

As can be seen from the PECAM-1 staining shown in FIGS. 2A–2F, the combined transfer of AdVEGF-$B_{167}$ and AdVEGF-A induced stronger formation of PECAM-1 positive vessels (FIGS. 2C and 2F) than AdVEGF-A alone (FIGS. 2B and 2E), while AdLacZ (FIGS. 2A and 2D) did not have any effects on the vasculature. The bar scale represents 100 micrometers.

For quantitation, the PECAM-1 positive vessels were counted at 200× magnification, using square grids (area= 0.16 $mm^2$, 20× magnification). The mean and p-values were calculated using the paired students t-test. Only values averaging higher than two standard deviations of the vessel number in the Lac virus-infected control sample were taken into consideration.

Figure 3:
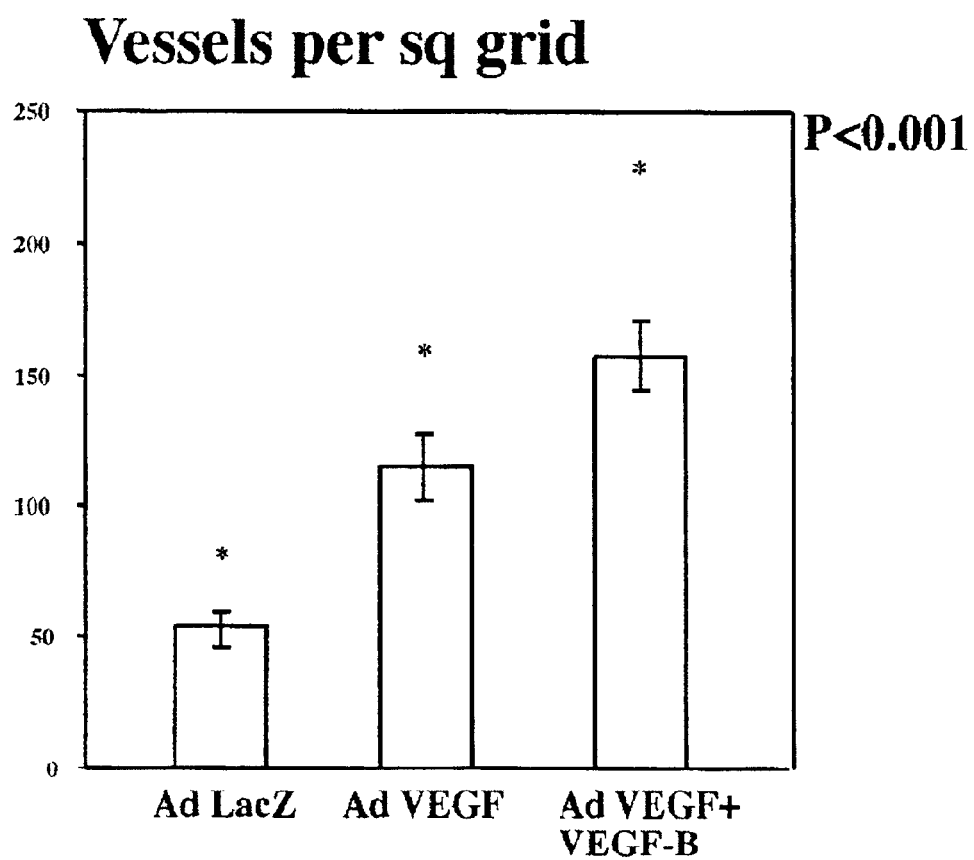
FIG. 3 provides quantitative results of blood vessel formation.

As can be seen in FIG. 3, combined gene transfer of AdVEGF-$B_{167}$ and AdVEGF-A induced an approximately threefold increase in blood vessel density and VEGF-A induced a two-fold increase of blood vessel density at $p<0.001$ in comparison to ears injected with AdVEGF-$B_{167}$ or AdLacZ alone. Thus VEGF-B potentiates the angiogenic effect of VEGF-A. It is within the scope of the invention to substitute full length, active fragments, or conservatively substituted sequences of VEGF-C or VEGF-D for VEGF-A and achieve similar results as noted above.

EXAMPLE 3

Administration of Adenoviruses According to the Present Invention

A first recombinant adenovirus comprising full length or active fragments of the VEGF-$B_{167}$ sequence is prepared as described above or following other acceptable methods in the art. Conservative substitutions may be made to the sequence. A second recombinant adenovirus comprising full length or active fragments of the VEGF-A, VEGF-C, or VEGF-D sequence is prepared as described above or following other acceptable methods in the art. Conservative substitutions may be made to the sequence.

Target cells are identified for administration of the two recombinant adenovirus vectors. For example, microvascular endothelial cells may be targeted. The two vectors are administered to the target cells by methods capable of transfecting the target cells with the two vectors. For example, injection of the vectors into the microvasculature. If desired, the organism comprising the target cells may be monitored or evaluated to determine the extent of stimulation of angiogenesis.

It may be desirable to introduce the recombinant adenovirus vectors to cells proximate to the endothelial cells. Any cell type susceptible to transfection and any method of transfection may be employed. VEGFs encoded by the vectors would be secreted by the transfected cells and cause the desired angiogenic stimulation in proximate endothelial cells. For example, in the ischemic leg model, a skeletal muscle cell could be targeted for adenovirus vector administration according to the present invention. Subsequent to transfection, the skeletal muscle cell(s) targeted would secrete the transfected VEGFs and induce cell growth and blood vessel formation in proximate endothelial cells.

The foregoing description and examples have been set forth merely to illustrate the invention and are not intended to be limiting. Since modifications of the disclosed embodiments incorporating the spirit and substance of the invention may occur to persons skilled in the art, the invention should be construed broadly to include all variations falling within the scope of the appended claims and equivalents thereof.

What is claimed is:

1. A method of stimulating angiogenesis in a mammal, comprising:
   introducing a first replication-deficient adenovirus vector comprising a polynucleotide sequence encoding VEGF-$B_{167}$ or a fragment or conservative substitution thereof to said mammal; and
   introducing a second replication-deficient adenovirus vector comprising a polynucleotide sequence encoding VEGF-A or a fragment or conservative substitution thereof to said mammal,
   wherein said first replication-deficient adenovirus vector and said second replication-deficient adenovirus vector are directly delivered to a site in said mammal where there is at least one living cell selected from the group consisting of endothelial cells and cells proximate to endothelial cells of said mammal, and
   wherein density of PECAM-1 positive vessels is increased in said site when compared to a site untreated or treated with VEGF-$B_{167}$ alone or VEGF-A alone.

2. The method according to claim 1, wherein said at least one living cell is a vascular cell.

3. The method according to claim 1, wherein said endothelial cells are microvascular endothelial cells.

4. The method according to claim 1, wherein said endothelial cells are aortic endothelial cells.

5. The method according to claim 1, wherein said mammal is murine.

6. The method according to claim 1, wherein said mammal is human.

7. The method according to claim 1, wherein $10^7$ to $10^{13}$ of vector particles of each adenovirus vector are introduced.

8. The method according to claim 1, wherein expression of the polynucleotide sequence in the first or second vector is driven by a CMV promoter.

9. A method of stimulating angiogenesis in a mammal, comprising:
   introducing a first replication-deficient adenovirus vector comprising a polynucleotide sequence encoding VEGF-$B_{167}$ or a fragment or conservative substitution thereof to said mammal; and
   introducing a second replication-deficient adenovirus vector comprising a polynucleotide sequence encoding VEGF-C or a fragment or conservative substitution thereof to said mammal,
   wherein said first replication-deficient adenovirus vector and said second replication-deficient adenovirus vector are directly delivered to a site in said mammal where there is at least one living cell selected from the group consisting of endothelial cells and cells proximate to endothelial cells of said mammal, and
   wherein density of PECAM-1 positive vessels is increased in said site when compared to a site untreated or treated with VEGF-$B_{167}$ alone or VEGF-C alone.

10. The method according to claim 9, wherein said at least one living cell is a vascular cell.

11. The method according to claim 9, wherein said endothelial cells are microvascular endothelial cells.

12. The method according to claim 9, wherein said endothelial cells are aortic endothelial cells.

13. The method according to claim 9, wherein said mammal is murine.

14. The method according to claim 9, wherein said mammal is human.

15. The method according to claim 9, wherein $10^7$ to $10^{13}$ of vector particles of each adenovirus vector are introduced.

16. The method according to claim 9, wherein expression of the polynucleotide sequence in the first or second vector is driven by a CMV promoter.

17. A method of stimulating angiogenesis in a mammal, comprising:
   introducing a first replication-deficient adenovirus vector comprising a polynucleotide sequence encoding VEGF-$B_{167}$ or a fragment or conservative substitution thereof to said mammal; and
   introducing a second replication-deficient adenovirus vector comprising a polynucleotide sequence encoding VEGF-D or a fragment or conservative substitution thereof to said mammal, wherein said first replication-deficient adenovirus vector and said second replication-deficient adenovirus vector are directly delivered to a site in said mammal where there is at least one living cell selected from the group consisting of endothelial cells and cells proximate to endothelial cells of said mammal, and wherein density of PECAM-1 positive vessels is increased in said site when compared to a site untreated or treated with VEGF-$B_{167}$ alone or VEGF-D alone.

18. The method according to claim 17, wherein said at least one living cell is a vascular cell.

19. The method according to claim 17, wherein said endothelial cells are microvascular endothelial cells.

20. The method according to claim 17, wherein said endothelial cells are aortic endothelial cells.

21. The method according to claim 17, wherein said mammal is murine.

22. The method according to claim 17, wherein said mammal is human.

23. The method according to claim 1, wherein $10^7$ to $10^{13}$ of vector particles of each adenovirus vector are introduced.

24. The method according to claim 1, wherein expression of the polynucleotide sequence in the first or second vector is driven by a CMV promoter.

* * * * *